United States Patent [19]

Konings et al.

[11] Patent Number: 4,888,284
[45] Date of Patent: Dec. 19, 1989

[54] DIPEPTIDASE, ITS ISOLATION FROM LACTIC ACID BACTERIA, ANTIBODIES AGAINST THE DIPEPTIDASE, THE USE OF THE DIPEPTIDASE AND OF THE ANTIBODIES AGAINST IT

[75] Inventors: Willem N. Konings, Haren; Aart van Boven, Groningen, both of Netherlands

[73] Assignee: Rijksuniversiteit te Groningen, Netherlands

[21] Appl. No.: 175,768

[22] Filed: Mar. 31, 1988

[30] Foreign Application Priority Data

Apr. 1, 1987 [NL] Netherlands .......................... 8700767

[51] Int. Cl.$^4$ ............................................. C12N 9/00
[52] U.S. Cl. ...................................... 435/183; 435/212; 435/814; 435/853
[58] Field of Search .................. 435/183, 814–816, 435/212, 853

[56] References Cited

U.S. PATENT DOCUMENTS 3,947,324  3/1976  Lakshminarayanan ............. 435/185
4,560,661 12/1985  Katsumata ........................... 435/183

Primary Examiner—Peter D. Rosenberg
Attorney, Agent, or Firm—Cooper & Dunham

[57] ABSTRACT

This invention relates to dipeptidase of lactic acid bacteria in isolated form, characterized by a molecular weight of 55 kD±5 kD; an isoelectric point of 4.4±0.4; a substrate range including the dipeptides leu-leu, leu-met, leu-val, leu-gly, val-leu, phe-leu and ala-ala, but not the dipeptides his-leu, γ-glu-leu, gly-leu, α-glu-ala and peptides of 3 or more amino acid residues; and a hydrolyzing activity with a temperature optimum at 50° C.±10° C., a pH optimum at 8±1, and sensitivity to the metal chelating EDTA and to the reducing agents dithiotreitol and mercaptoethanol. The invention also relates to a process for isolating the dipeptidase from lactic acid bacteria; to the use of the dipeptidsae for preparing polyclonal or monoclonal antibodies having an affinity to, and/or specificity for, the dipeptidase; to polyclonal and monoclonal antibodies having an affinity to, and/or specificity for, the dipeptidase; to the use of polyclonal or monoclonal antibodies for detecting the dipeptidase in, or removing or isolating it from, a mixture containing the dipeptidase; to the use of the dipeptidase in the production of food products, and to food products produced using the dipeptidase.

12 Claims, 4 Drawing Sheets

DIPEPTIDASE, ITS ISOLATION FROM LACTIC ACID BACTERIA, ANTIBODIES AGAINST THE DIPEPTIDASE, THE USE OF THE DIPEPTIDASE AND OF THE ANTIBODIES AGAINST IT

This invention relates to a dipeptidase from lactic acid bacteria in the isolated form, i.e., in a substantially pure state relatively to the state in which it is present in vivo in lactic acid bacteria.

Lactic acid bacteria, in particular lactic acid Streptococci, such as *Streptococcus cremoris, Streptococcus lactis* and *Streptococcus diacetylactis*, as well as other lactic acid bacteria, such as Leuconostoc species, are used on a large scale in the food industry, in particular in the dairy industry for preparing fermented milk products, such as cheese. Owing to the production of lactic acid from lactose, the food product is acidified, thereby preventing deterioration of the product. Moreover, the bacteria are involved in the development of the flavour and taste of the food product. One important process therein is the decomposition of proteins.

For growth and for lactic acid production, the bacteria need a nutrient medium which provides essential growth factors, such as vitamins and amino acids. Milk is a suitable nutrient medium and enables growth to high cell densities. The milk's content of free amino acids, however, is insufficient for this purpose, so that for their supply of amino acids, the bacteria are dependent on their proteolytic system for the breakdown of milk proteins, in articular casein. The proteolytic system of lactic acid bacteria remains active even after their growth has ceased, e.g., in the cheese ripening phase, in which the decomposition of casein to peptides and subsequently amino acids contributes to the flavour development of the cheese.

The proteolytic system of lactic acid streptococci comprises different proteases and different peptidases. The proteases are localized in the cell wall of the bacteria, whereas the peptidases may be present in the cytoplasmic membrane and within the cell.

Hitherto, only a few peptidases from streptococci have been isolated and characterized. Hwang et al., Agric. Biol. Chem. 45 (1981) 159–165 and 46 (1982) 3049 3053 have isolated a dipeptidase with a broad substrate specificity from *Streptococcus cremoris* H61. Geis et al., Appl. Microbiol. Biotechnol. 23 (1985) 79–84 have extracted and purified a cell-wall associated aminopeptidase from *S. cremoris* AC1. Desmazeaud and Zevaco, Milchwissenschaft 34 (1979) 606–610 have isolated two intracellular aminopeptidases from *S. diacetylactis*.

In the Dutch cheese industry, *S. cremoris* is the most important lactic acid bacterium. A good insight in the proteolytic system of lactic acid streptococci, such as *S. cremoris*, can contribute towards an improvement of the starter cultures and towards a better regulation of the ripening process, so that, for example, accelerated cheese ripening can be realized or the formation of a bitter note can be prevented. Much basic information is given in the thesis by R. Otto: "An ecophysiological study of starter streptococci", Groningen State University (1981), and in the thesis by J. Hugenholtz: "Population dynamics of mixed starter cultures", Groningen State University (1986). In the latter thesis, a study into the proteases of *S. cremoris* Wg2 is described.

The present invention is based on a study into the peptidases of *S. cremoris* Wg2, in which a specific dipeptidase not so far described has been isolated and characterized. The dipeptidase was purified from a crude cell-free extract of *S. cremoris* Wg2 by DEAE-Sephacel column chromatography, followed by preparative electrophoresis. The dipeptidase exhibits hydrolytic activity with respect to several dipeptides and, in view of its sensitivity to the metal chelates forming compound EDTA, is a metallo-enzyme exhibiting a pH optimum at about 8 and a temperature optimum at about 50° C. SDS-PAA gel electrophoresis of the purified enzyme shows one single protein band with a molecular weight of about 55 kD. The enzyme experiences strong inhibition from compounds such as mercaptoethanol and dithiotreitol, which are capable of reducing disulfide bonds, and is insensitive to sulfhydryl group reagents, such as naphthyl maleimide, iodo-acetic acid and 5, 5-dithio-bis(2-nitrobenzoic acid). A kinetics examination of the leucyl-leucine and alanylalanine hydrolysis shows that the enzyme has a relatively low affinity to these substrates ($K_m$ 1.6 and 7.9 mM, respectively), but has very high maximum rates of hydrolysis ($V_{max}$ 3700 and 13000 /moles/min. mg protein, respectively). These values correspond with turnover numbers of about 3000 and about 1000 $sec^{-1}$, respectively. The pI (isoelectric point) of the enzyme is relatively low (about 4.4), which explains that the enzyme can be purified by means of preparative PAA gel electrophoresis.

The new dipeptidase according to this invention is distinguished from the dipeptidase isolated from *S. cremoris* H61 by Hwang et al. in molecular weight, substrate specificity and peptide hydrolysis rates, and differs at least in substrate specificity from the earlier described aminopeptidases. The new dipeptidase hydrolyzes several dipeptides, including leu-leu, leu-met, leu-val, leu-gly, val-leu, phe-leu and ala-ala. On the other hand, the new dipeptidase is found to be incapable of significantly hydrolyzing dipeptides, such as his-leu, γ-glu-leu, gly-leu, α-glu-ala, and pro-leu, which contain proline, histidine, glycine, or glutamate as the N-terminal amino acid, any more than hydrolyzing tripeptides, tetrapeptides and higher polypeptides.

The new dipeptidase according to this invention has in common with the earlier described known peptidases from lactic acid streptococci that the metal chelating agent EDTA gives a strong inhibition of hydrolytic activity, which activity can subsequently be restored by adding certain bivalent cations, such as $Co^{++}$ and $Mn^{++}$. Surprisingly, however, higher concentrations of $Co^{++}$ turn out to have again an inhibitory effect.

The rate of hydrolysis of the new dipeptidase is much higher than the rate at which the cells take up peptides, so that the peptide uptake is a velocity limiting step in the degradation of the peptide by the streptococci. This implies, for example, that accelerated cheese ripening can be realized if the bacteria export peptidases from the cell, or if purified peptidase is added to the medium.

The new dipeptidase could also be used to prevent the formation of an undesirable bitter taste during cheese ripening. In fact, some *S. cremoris* strains are found to produce various grades of bitterness after the decomposition of casein, evidently as a result of the collection of peptides with a high content of hydrophobic amino acids, which are only slowly broken down by the peptidases of the bacteria present in the starter composition. The use of the present dipeptidase could mitigate this problem.

Further possible uses of the dipeptidase for other purposes are the clarification of beer and soft drinks, and also, of course, its use in DNA technology in the broad sense of the word.

The invention is in the first place embodied in the dipeptidase proper, i.e., a dipeptidase from lactic acid bacteria in the isolated form, characterized by a molecular weight of 55 kD±5 kD; an isoelectric point of 4.4±0.4; a substrate range including the dipeptides leu-leu, leu-met, leu-val, leu-gly, val-leu, phe-leu and ala-ala, but not the dipeptides his-leu, γ-glu-leu, gly-leu, α-glu-ala and peptides from three or more amino acid residues; and a hydrolytic activity with a temperature optimum at 50° C.±10° C., a pH optimum at 8±1, and sensitivity to the metal chelates forming EDTA and to the reducing agents dithiotreitol and mercaptoethanol.

Although the dipeptidase factually isolated and characterized according to the experimental section herein comes from one specific organism, namely a proteinase negative variant of *S. cremoris* Wg2, the invention also covers the corresponding dipeptidases from other lactic acid bacteria, as these have corresponding properties and can be isolated from the bacteria and purified in a similar manner. "Corresponding dipeptidases" as used above does not mean that the peptidases are exactly equal, i.e., have the same amino acids sequence, but rather means that they satisfy the above characterization of the dipeptidase.

A more specific embodiment of the invention concerns the dipeptidase from lactic acid streptococci, in particular *S. cremoris*, preferably *S. cremoris* Wg2.

The words "in isolated form" and "from" are not intended to limit the invention to dipeptidase isolated from its natural ambient. In fact, the invention creates the possibility of tracing the dipeptidase gene and subsequently realizing production of the dipeptidase in transformed cells or organisms by means of recombinant DNA technology. For this purpose, for example, first the amino acid sequence of the dipeptidase, or of a part thereof, could be determined. On the basis thereof, corresponding DNA sequences can be derived by means of the genetic code, whereafter suitable DNA probes can be synthesized with which dipeptidase messenger RNA (mRNA) of the cells can be detected and isolated. This mRNA can be used by methods known per se for preparing copy DNA (cDNA) using enzymes such as reverse transcriptase and DNA polymerase. This cDNA can then, by means of suitable vectors (mostly plasmids) be cloned and expressed in suitable host cells, from which the dipeptidase produced can be readily recovered.

The invention also creates the possibility of producing antibodies against the dipeptidase and subsequently using these for removing or isolating the dipeptidase from its natural surroundings or from the above transformed cells or organisms.

The invention is accordingly also embodied in the use of the new dipeptidase for the preparation of polyclonal or monoclonal antibodies with an affinity to, and/or specificity for, the dipeptidase, in the polyclonal and monoclonal antibodies proper, and in their use for detecting the dipeptidase in, or removing or isolating it from, a mixture comprising the dipeptidase.

Naturally the invention is further embodied in the use of the new dipeptidase in the production of food products, such as cheese, beatable products and meat products, using the hydrolytic properties of the dipeptidase, e.g., for realizing accelerated cheese ripening or preventing the formation of a bitter flavour. The food products thus obtained are also covered by the invention.

The invention is further embodied in a process for isolating the new dipeptidase from lactic acid bacteria, which comprises subjecting a crude cell-free extract from the lactic acid bacteria to ion exchange column chromatography, subjecting one or more fractions with leucyl-leucine hydrolytic activity to electrophoresis, and recovering one or more fractions with leucyl-leucine hydrolytic activity.

In a preferred embodiment of this process, the ion exchange column used is a DEAE-Sephacel column, and fractionation is realized by gradient elution. The electrophoresis is preferably a preparative polyacrylamide gel electrophoresis formed in a column, with the effluent from the column being collected in fractions.

The invention is illustrated in and by the following experimental section and the accompanying drawings.

●—●: protein content ($A_{280}$)

o—o: leucyl-leucine peptidase activity, measured by the Cd/ninhydrine method x—x: NaCl concentration. The fractions 148–175 were combined.

Figure 3:
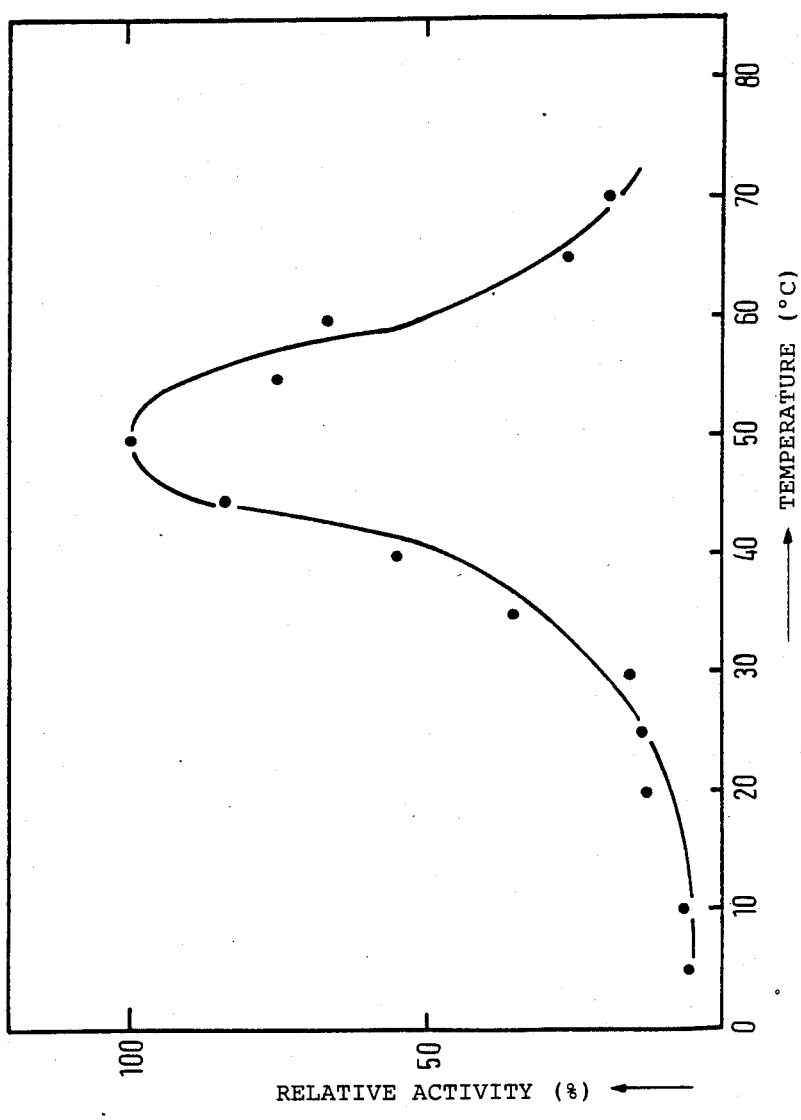

FIG. 3 shows the effect of the temperature on the leucyl-leucine activity in 20 mM HEPES pH 7.8, determined by the Cd/ninhydrine method.

Figure 4:
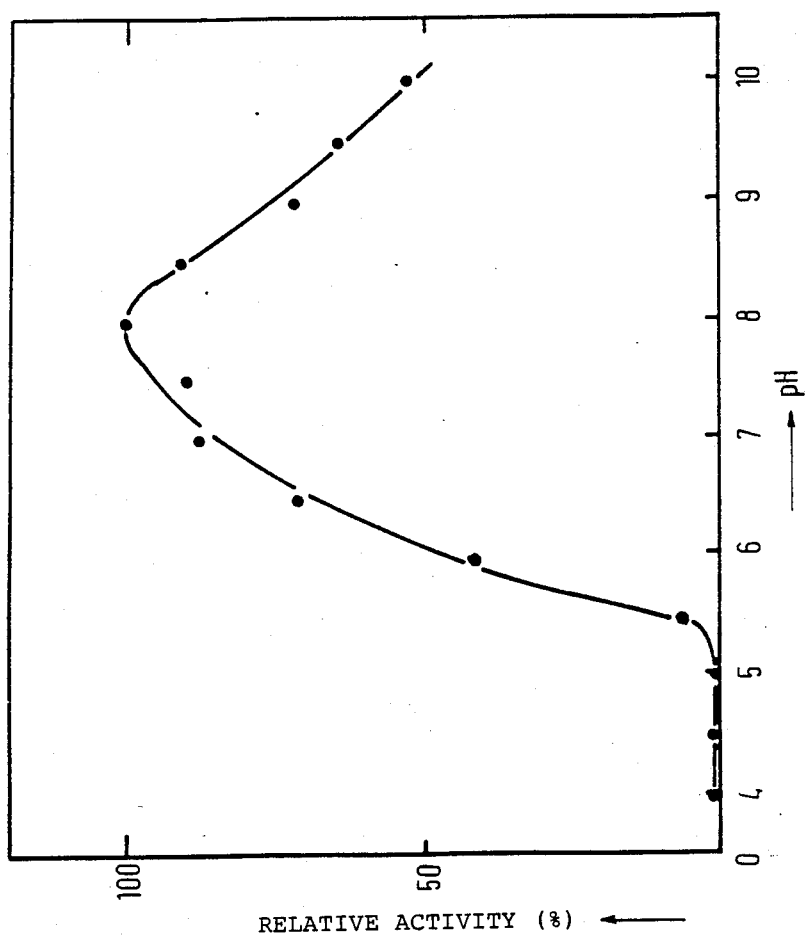

FIG. 4 shows the effect of the pH on the peptidase activity, measured in 20 mM malic acid, 20 mM MES, 20 mM HEPES and 20 mM boric acid, adjusted with KOH to different pH values. The peptidase activity was determined with leucyl-leucine by the Cd/ninhydrine method.

Figure 5:
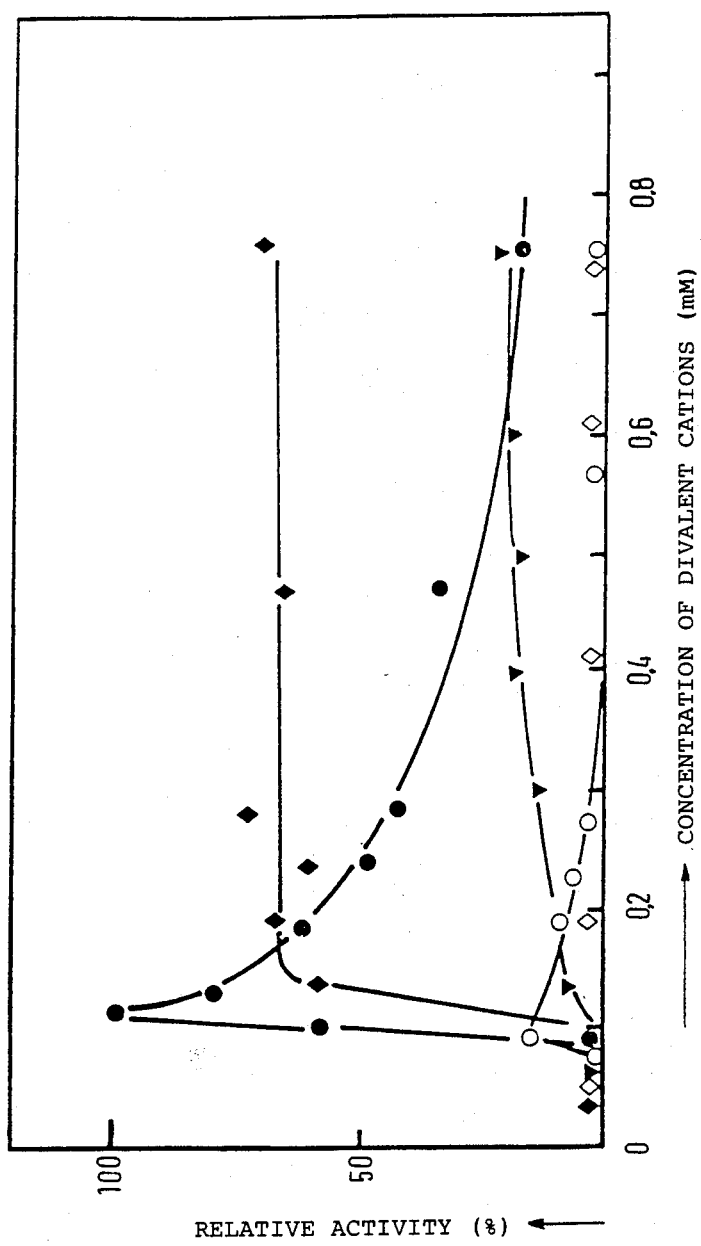

FIG. 5 shows the reactivation of the EDTA-treated dipeptidase with bivalent cations: ( )$Mn^{++}$; (●)$Co^{++}$; (O)$Zn^{++}$;( )$Ca^{++}$; ( )$Cu^{++}$.

Materials and methods

Organism and preparation of a cell-free extract

In the experiments, a proteinase-negative variant of *S. cremoris* Wg2 was used. The organism was routinely kept in 10% (wt./vol.) sterile reconstituted skim milk containing 0.1% (wt./vol.) trypton, at a temperature of −20° C.. For the cultivation of *S. cremoris* Wg2, MRS broth (De Man et al., J. Appl. Bacteriol. 23 (1960), 130–135) was used, which was grown at a controlled pH of 6.3 in a 5-liter fermenter. Membrane vesicles of *S. cremoris* Wg2 were isolated as described by Otto et al., J. Bacteriol. 149 (1982), 733–738. The supernatant obtained by removing the membrane vesicles and whole cells from the lysozyme treated cell suspension was used as the crude cell-free extract.

Enzyme assays (i) Leucyl-leucine hydrolysis activities were determined by measuring the release of leucine by means of the modified Cd-ninhydrin method, described by Van Boven and Konings, Appl. Environ. Microbiol. 51 (1986), 95–100.

(ii) The hydrolysis of alanine containing peptides was determined by measuring the release of alanine by means of a coupled enzyme reaction according to Grassl (1974) (L-alanine determination with GPT and LDH, pp 1682–1685 (in H. U. Bergmeyer (ed.), Methods in enzymatic analysis, Academic Press, Inc., New York, San Francisco and London). The reaction mixture contained, in a total volume of 1 ml 0.1M Tris-HCl pH 7.6, 50 μl of a suitable amount of enzyme, 100 μl 0.2M oxo-glutaric acid, 50 μl 12 mM NADH, 10 μl lactate-dehydrogenase (1 mg/ml in 3.2M $(NH_4)_2SO_4$) and 25 μl glutamate pyruvate transaminase (8 mg/ml in 3.2M $(NH_4)_2SO_4$). The reaction was started by adding 20 μl peptide solution and hydrolysis of peptides was continuously monitored by means of a double-beam spectrophotometer as the decrease of NADH at 340 nm. Enzyme activities were calculated using a molar absorption coefficient for NADH of $6.22 \times 10^3$ $M^{-1}cm^{-1}$.

(iii) The hydrolysis of leucine containing peptides was determined by measuring the release of leucine. The amount of leucine can be detected in a coupled enzyme reaction in which o-dianisidine (reduced) is oxidized. The reaction mixture contains, in a total volume of 1 ml, 0.2M tri-ethanolamine pH 7.6, 50 μl of an appropriate amount of enzyme, 5 μl 23.2 mM o-dianisidine (in 0.5 N HCl), 5 μl horseradish peroxidase (10 mg/ml in 3.2M $(NH_4)_2SO_4$) and 30 μl L-amino acid oxidase. The reaction was started by adding 20 μl peptide solution, and hydrolysis was continuously monitored spectrophotometrically as the amount of oxidized o-dianisidine formed at 436 nm. Enzyme activities were calculated using a molar absorption coefficient for oxidized o-dianisidine of $8.1 \times 10^3 \, M^{-1}cm^{-1}$.

(iv) The hydrolysis of leucyl-p-nitroanilide was determined by the method of Exterkate, Neth. Milk Diary J. 29 (1975), 303–318. Leucyl-p-nitroanilide (200 μl 2 mM) was incubated with an appropriate amount of enzyme for 40 minutes. The reaction was stopped after the addition of 200 μl 30% acetic acid, and the amount of nitroanilide was measured at 410 nm.

All measurements of enzyme activities were performed at 30° C., unless stated otherwise.

DEAE-Sepahcel column chromatography

A DEAE-Sephacel column (3.2×20 cm) was equilibrated with 10 mM $K_2HPO_4/KH_2PO_4$ pH 7.0 with 0.12M NaCl. The cell-free extract obtained after the isolation of membrane vesicles of *S. cremoris* Wg2 was diluted with destilled water to the same strength as the buffer used for equilibrating the DEAE-Sephacel column, and was subsequently applied to the column. After washing the column with 2 volumes of equilibration buffer, the enzyme was eluted with a linear gradient of 0.12–0.3M NaCl in the same buffer. Fractions of 2.5 ml were collected and tested for leucyl-leucine hydrolysis activity by the Cd-ninhydrine method. The fractions with the highest enzyme activity were combined.

Preparative electrophoresis

Figure 1:
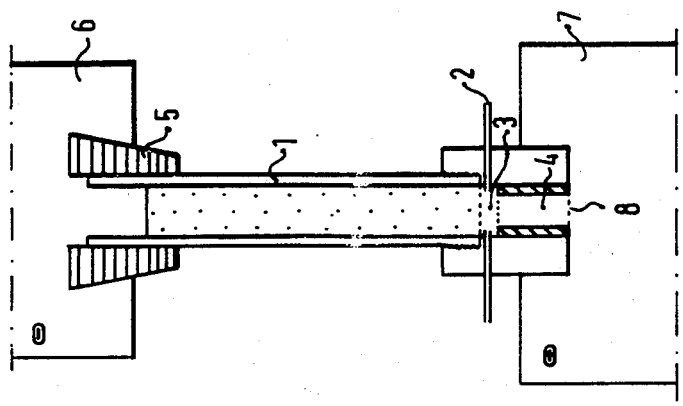
FIG. 1 diagramatically shows the experimental set-up used for the preparative electrophoresis. The PAA column is designated by reference numeral 1, the buffer stream by reference numeral 2, the elution chamber by reference numeral 3, the agarose by reference numeral 4, the rubber stopper by reference numeral 5, the negative side of the buffer reservoir by reference numeral 6, the positive side of the buffer reservoir by reference numeral 7, and the dialysis membrane by reference numeral 8.

The experimental set-up used for the preparative PAA-gel electrophoresis (using a 7.5% PAA column, 1.5×14 cm) is shown schematically in FIG. 1. By electrophoresis the proteins are separated on the PAA column. These proteins are eluted from the column and collected by a constant flow of buffer at the end of the column, transverse to the direction of electrophoresis. Peptidase containing fractions obtained from the DEAE-Sephacel column were concentrated to 0.2 ml (19.8 mg protein) mixed 1 : 1 with sample buffer (25 mM Tris-borate pH 8.0, 18% glycerol and 0.01% Bromphenol blue) and applied to the PAA column. Electrophoresis was started with a constant current of 4 mA. The Bromphenol blue reached the end of the column after 15 hours of electrophoresis. A constant stream (0.2 ml/min) of buffer (25 mM Trisborate pH 8.0) was pumped through the elution chamber, connected to the PAA column, and electrophoresis was continued for another 10 hours at a constant current of 40 mA. Fractions of 5 ml were collected from the eluate of the elution chamber and tested for leucyl-leucine hydrolyzing activity by the Cd-ninhydrine method. Fractions having the highest enzyme activities were combined.

SDS-PAA gel electrophoresis

Sodium dodecyl sulphate (SDS)-polyacrylamide (PAA) gel electrophoresis was performed as described by Laemmli and Faure, J. Mol. Biol. 80 (1973), 575–599. The protein samples were mixed 1 : 1 with sample buffer (0.18M Tris-HCl pH 6.8, 0.3% SDS, 8.6% glycerol, 10% mercaptoethanol and 0.07% Bromphenol blue) and applied to the gels.

The molecular weight of the enzymes was estimated by means of the following reference proteins: phosphorylase B (92.5 kD), bovine serum albumine (66.2 kD), ovalbumine (45.0 kD), carbonic anhydrase (31.0 kD), soy bean trypsine (21.5 kD) and lysozyme (14.4 kD).

Silver staining of the gels was performed according to Wray et al., Anal. Biochem. 118 (1981), 197–203. -20

CIE

Crossed immuno electrophoresis (CIE) was performed as described by Van der Plas et al., J. Bacteriol. 153 (1983), 1027–1037. The second dimension was performed at 2.5 V/cm for 10–15 hours. The CIE gels were stained with 0.5% Coomassie brilliant blue or with the zymogram staining technique for peptidase activities as described by Van Boven and Konings, loc. cit.

PAA/CIE

PAA gel electrophoresis was performed with a 7.5% PAA gel. Of the combined DEAE fractions, 0.75 mg protein was diluted 1:1 with sample buffer (without SDS) and applied to the gel. After 8 hours' of electrophoresis, one lane was silver-stained. The second lane was used as the first CIE dimension, applied to a glass plate (5×10 cm) and embedded in 6 ml 1% agarose containing antibodies against a cell-free extract of *S. cremoris* Wg2. The second dimension was performed as described for CIE, and the gel was stained using the zymogram technique for peptidase activity.

Isoelectric focusing

Isoelectric focusing (IEF) on slab gels was performed on "ready to use" Servalyt Precotes pH 3–10 (Serva Heidelberg, West Germany). The isoelectric point of the enzyme was determined using the following references: glycose oxidase (pI=4.15), bovine serum albumine (pI=4.7), carboxy anhydrase (pI=6.5) and cytochrome c (pI=10.65).

Amino acid analysis

Amino acid analysis of the purified enzyme was performed using a Kontron Liquimat III amino acid analyzer.

Effect of bivalent cations and chemical reactants on enzyme activity

Purified enzyme (116 μg) was incubated with 0.25 mM EDTA at 20° C. for 10 minutes. Excess EDTA was removed by dialysis against 20 mM N-2-hydroxyethyl piperazine-N'-2-morpholinoethane sulfonic acid (HEPES), pH 7.8, for 30 hours with two buffer changes. The EDTA-treated enzyme was pre-incubated with different concentrations of different bivalent cations in 200 μl 20 mM HEPES pH 7.8 at 20° C. for 10 minutes. Enzyme activities were determined with leucyl-leucine as the substrate using the Cd-ninhydrine method.

The effects of chemical reactants were determined by incubating 200 μl of a suitable enzyme solution with different chemicals at 20o C for 10 minutes. After the addition of leucyl-leucine, enzyme activity was determined using the Cd-ninhydrine method.

The effect of oxidizing and reducing reagents on enzyme activities

Purified enzyme was pre-incubated with ferric cyanide or oxidized glutathion for 5 minutes to produce oxidizing conditions and with dithiotreitol (DTT) or reduced glutathion to produce reducing conditions. 2 mM leucyl-leucine was added and peptide hydrolysis was stopped after 45 minutes by adding 3.5 mM mercaptoethanol. The reaction mixture was diluted 40-fold in 40 mM $Na_2CO_3$ pH 9.5, and the peptides were dansylated by mixing the samples with equal volumes of 1.5 mg/ml dansylchloride in acetonitrile. The amount of dansylated peptides was determined by reversed-phase HPLC on a $C_{18}$ column.

Protein determination

Unless otherwise stated, protein concentrations were determined by the method of Lowry et al., J. Mol. Chem. 193 (1951), 265–275, using bovine serum albumine as a standard.

Chemicals

All chemicals used were commercially available substances.

RESULTS

Enzyme purification

Step a.

Figure 2:
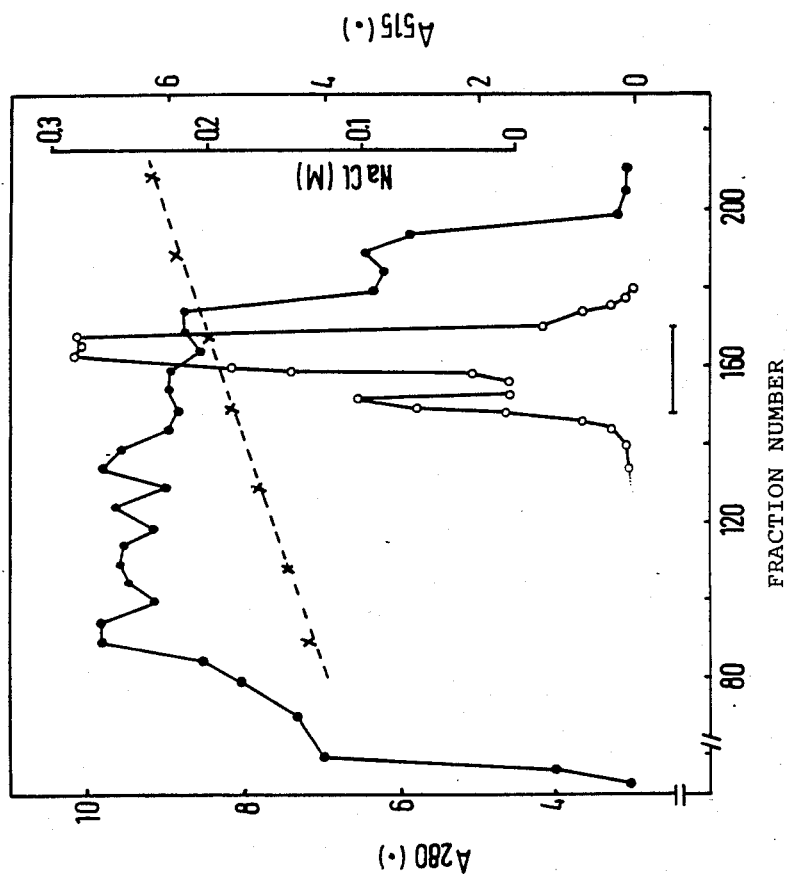
FIG. 2 shows the results of DEAE-Sephacel column chromatography of a crude cell-free extract of *S. cremoris* Wg2.

The crude cell-free extract was applied to a DEAE-Sephacel column. After elution with an NaCl gradient, the highest leucyl-leucine hydrolyzing activities were obtained in the fractions numbered 150 to 175 (FIG. 2) corresponding to 0.18–0.19M NaCl. These fractions were combined and after dialysis of the fractions against 10 mM $KH_2PO_4 K_2HPO_4$ pH 7.0, to remove NaCl, once more applied to a DEAE-Sephacel column. Fractions with leu-leu hydrolyzing activities were combined and concentrated in an Amicon filtration unit with a PM-10 membrane (10,000 molecular weight cut-off).

Step b.

After electrophoresis of this concentrated sample on a non-denaturing PAA-gel, the leucyl-leucine hydrolyzing enzyme was found by PAA/CIE experiments at the positive side of the gel. The enzyme was therefore purified further by preparative electrophoresis. Fractions containing leu-leu hydrolyzing activities were combined and concentrated to 7.5 ml.

Table A gives a summary of the enzyme purification. This table shows that the enzyme was purified 1240-fold with a yield of 21.5% from the crude cell-free extract.

The purified enzyme fraction obtained after preparative electrophoresis exhibited one single band in SDS/PAA gel electrophoresis when the gel was silver-stained, which indicates a highly purified enzyme (the contaminations in the SDS/PAA gel are due to the sample buffer). This was confirmed with CIE experiments of the purified enzyme. Throughout the entire range of precipitation lines in a CIE pattern of a cell-free extract against antibodies induced with a cell-free extract as antigen, only one precipitation line exhibited leucyl-leucine activity. When the purified enzyme was used as the antigen, one precipitation line was observed with leucyl-leucine hydrolyzing activity.

Molecular weight and isoelectric point

The molecular weight was estimated at 55,000 by SDS/PAA gel electrophoresis and by gel filtration on a Sephadex G-100 column. The identical results obtained under denaturing and natural conditions indicate that the enzyme is a monomer consisting of one single subunit.

The isoelectric point of the enzyme was estimated to be 4.4 by isoelectric focusing on slab gels with pH 3–10.

Temperature dependence and effect of pH on enzyme activity

The temperature dependence was determined by measuring the leucyl-leucine hydrolyzing activity in a range of 5°–70° C. by means of the Cd-ninhydrine method. The enzyme mixture was equilibrated at test temperatures before leucyl-leucine was added. The optimum temperature for leucyl-leucine hydrolyzing activity was found to be approximately 50° C. (see FIG. 3). At 70° C., still 15% of the optimum activity was found.

The effect of the pH was determined in a range of pH 4–10 in a buffer consisting of 20 mM each of malic acid, 2-N-morpholinoethane sulfonic acid (MES), HEPES and boric acid, adjusted to the selected pH values (see FIG. 4). The optimum pH for the hydrolysis of leucyl-leucine, as determined by the Cd-ninhydrine method, turned out to be approximately 8. At pH values below 5, no hydrolyzing activity of the enzyme could be detected, while at pH 10 about 50% of the activity was found.

Amino acid analysis

The amino acid composition of the enzyme is presented in Table B. The enzyme contains a very slight quantity of tyrosine and tryptophan, which explains the difficulties in determining the amount of purified enzyme with a Lowry protein assay.

Substrate specificity

The hydrolytic action of the enzyme on various peptides was examined. The activities were determined by measuring the release of leucine or alanine by a coupled enzyme reaction. Table C shows the relative rate of hydrolysis of different peptides. The enzyme was active towards various dipeptides with relatively hydrophobic and neutral aminoterminal amino acids, which suggests that the N-terminal amino acid of a peptide plays an important role in the specificity. Peptides of different compositions containing three or more amino acids were not hydrolyzed. On the other hand, most of the peptides tested were hydrolyzed by the cell-free extract. The C-terminal amino acids were also found to be of importance for the enzyme-substrate interaction. The hydrolyzing activity was determined using leucyl-p-nitroanalide as the substrate. Table D compares the activity of leucyl-p-nitroanilide hydrolysis of the several stages in the enzyme purification. The cell-free extract and the fractions obtained from the second DEAE-Sephacel column hydrolyze leucyl-p-nitroanilide, but the purified enzyme was found to be unable to hydrolyze this substrate, which indicates that the C-terminal amino acids of a dipeptide are also determinative of the specificity of the enzyme. Peptides containing modified peptide bonds could not be hydrolyzed, either by the cell-free extract, or by the purified enzyme.

From these observations, it was concluded that the enzyme has a preference for certain dipeptides which it can hydrolyze, and for this reason can be called a dipeptidase.

Effects of metal ions on enzyme activity

After a treatment of the enzyme with the metal chelating agent EDTA, the activity was completely inhibited. The addition of 100 $\mu$M $CoCl_2$ or $MnCl_2$ restored the activity (see FIG. 5). The most effective metal ion turned out to be $Co^{++}$, but at concentrations above 200 $\mu$M, $Co^{++}$ became inhibitory. On the other hand, stimulation with $MnCl_2$ was maximal at concentrations above 200 $\mu$M and up to 750 $\mu$M no inhibitory effect on enzyme activity was observed. $ZnCl_2$ or $CaCl_2$ also showed a stimulation of enzyme activity, albeit to a lesser extent. $CuCl_2$ was unable to restore enzyme activity. All metal ions were added as chloride salts to prevent any influence of the anions. The results show that the dipeptidase activity is dependent on bivalent metal ions.

Effect of other potential inhibitors

Various sulfhydryl group and disulfide group reagents were tested for inhibition of dipeptidase activity. Dipeptidase activity was strongly inhibited by DTT or mercaptoethanol, which can reduce disulfide bonds in the enzyme (see Table E). The addition of sulfhydryl group reagents, such as naphthyl maleimide, iodo-acetic acid and 5, 5-dithio-bis(2-nitrobenzoic acid) had no inhibitory effect on the dipeptidase activity. Phenylarsenic oxide, a sulfhydryl reagent, had no inhibitory effect either. p-Chloromercuribenzoate, on the other hand, exhibited an inhibition of dipeptidase activity, probably because of a very aspecific inhibition. These results suggest that the hydrolyzing activity of the dipeptidase depends on the oxidized/reduced state of the enzyme. This was confirmed by experiments in which the dipeptidase activity was reduced by adding DTT, followed by reoxidation with ferric cyanide (Table F). Oxidation of the dipeptidase had no effect on the activity, but reduction with DTT showed a strong inhibition of the activity, which thereafter could be restored by ferric cyanide. Manipulation of the redox state of the enzyme with oxidized and reduced glutathion also indicated that optimal leucyl-leucine hydrolysis occurs when the dispeptidase is in the oxidized form.

TABLE A

Purification of a leu-leu dipeptidase of S. Cremoris Wg2.

| Purification step | volume (ml) | total protein (mg) | total activity[a] ($\times 10^{-5}$) | yield (%) | spec. activity[b] ($\times 10^{-5}$) | purification |
|---|---|---|---|---|---|---|
| cell-free extract | 1120 | 2508 | 15.37 | 100 | 0.006 | 1 |
| I DEAE Sephacel | 70 | 118.3 | 4.28 | 27.8 | 0.036 | 6 |
| II DEAE Sephacel | 33 | 59.4 | 3.56 | 23.1 | 0.059 | 10 |
| tube-current electrophoresis | 7,5 | 0.44* | 3.30 | 21.5 | 7.60 | 1239 |

[a] total activity is expressed as nmoles leucyl-leucine hydrolyzed per minute
[b] the specific activity is expressed as nmoles leucyl-leucine hydrolyzed per mg protein per minute.
*the protein concentration was estimated from the amino acid composition of the enzyme, the molecular weight and the amount of sample injected into the amino acid analyzer.

TABLE B

Amino acid composition of a dipeptidase of S. cremoris Wg2.

| Amino acid | Percentage | number of amino acid residues per enzyme molecule[a] |
|---|---|---|
| Aspartate | 10.42 | 38 |
| Threonine | 3.84 | 15 |
| Serine | 5.16 | 24 |
| Glutamic acid | 12.51 | 41 |
| Proline | 6.19 | 26 |
| Glycine | 13.84 | 90 |
| Alanine | 8.86 | 93 |
| Cysteine | 0.96 | 4 |
| Valine | 5.49 | 23 |
| Methionine | 3.14 | 10 |
| Isoleucine | 3.71 | 14 |
| Leucine | 9.86 | 37 |
| Tyrosine | 2.50 | 7 |
| Phenylalanine | 2.55 | 7 |
| Lysine | 5.94 | 20 |
| Histidine | 2.27 | 7 |
| Arginine | 2.64 | 7 |
| Tryptophan | N.D. | N.D. |

[a] the molecular weight of the enzyme was estimated to be 55,000
N.D. = not detectable

TABLE C

Substrate specificity of a dipeptidase of S. cremoris Wg2

| Substrate (2 mM) | Peptidase hydrolysis (%) | Cell-free extract hydrolysis (%) |
|---|---|---|
| leu-leu | 100 | 100 |
| leu-met | 440 | 240 |
| leu-val | 25 | 120 |
| leu-gly | 83 | 132 |
| val-leu | 33 | 140 |
| phe-leu | 170 | 178 |
| pro-leu | 2 | 10 |

TABLE C-continued

Substrate specificity of a dipeptidase of S. cremoris Wg2

| Substrate (2 mM) | Peptidase hydrolysis (%) | Cell-free extract hydrolysis (%) |
|---|---|---|
| his-leu | 0 | 10 |
| γ-glu-leu | 0 | 0 |
| gly-leu | 0 | 12 |
| ala-ala | 140 | 43 |
| α-glu-ala | 0 | 28 |
| leu-leu-leu | 0 | 88 |
| leu-gly-gly | 0 | 38 |
| ala-ala-ala | 0 | 18 |
| (ala)$_4$ | 0 | 11 |
| (ala)$_6$ | 0 | 0 |

TABLE D

Hydrolysis of leucyl-p-nitroanilide and leucyl-leucine in different stages of the purification procedure of a dipeptidase of S. cremoris Wg2.

| Purification step | Leucyl-p-nitroanilide hydrolysis | Leucyl-leucine hydrolysis |
|---|---|---|
| cell-free extract | ++ | ++ |
| second DEAE Sephacel column | ++ | ++ |
| preparative electrophoresis | − | ++ |

TABLE E

Inhibition of dipeptidase activity

| Inhibitor (1 mM) | Relative activity |
|---|---|
| no addition | 100 |
| DTT | 20 |
| Mercaptoethanol | 15 |
| Phenyl arsenic oxide | 100 |
| Iodo-acetic acid | 105 |
| Naphthyl maleimide | 90 |
| 5,5-dithio-bis(2-nitrobenzoic acid) | 100 |
| p-chloromercuribenzoate | 20 |

TABLE F

Dipeptidase activity under oxidized and reduced conditions

| Addition | Leucyl-leucine (mM)* | Relative quantity of hydrolyzed leucyl-leucine (%) |
|---|---|---|
| none | 2.7 | 0 |
| dipeptidase | 1.2 | 100 |
| dipeptidase + 1 mM Fe$_3$(CN)$_6$ | 1.4 | 85 |
| dipeptidase + 5 mM Fe$_3$(CN)$_6$ | 1.2 | 100 |
| dipeptidase + 2 mM DTT | 2.7 | 0 |
| dipeptidase + 2 mM DTT + 1 mM Fe$_3$(CN)$_6$ | 2.2 | 35 |
| dipeptidase + 2 mM DTT + 5 mM Fe$_3$(CN)$_6$ | 1.4 | 85 |
| dipeptidase + 2 mM GSSG | 1.1 | 105 |
| dipeptidase + 2 mM GSH | 1.8 | 60 |

*mM leucyl-leucine remaining behind in the incubation mixture after hydrolysis

What we claim:

1. Dipeptidase of lactic acid bacteria in isolated form, characterized by a molecular weight of 55 kD±5 kD; an isoelectric point of 4.4±0.4; a substrate range including the dipeptides leu-leu, leu-met, leu-val, leu-gly, val-leu, phe-leu and ala-ala, but not the dipeptides his-leu, γ-glu-leu, gly-leu, α-glu-ala and peptides of 3 or more amino acid residues; and a hydrolyzing activity with a temperature optimum at 50° C.±10° C., a pH optimum at 8±1, and sensitivity to the metal chelating EDTA and to the reducing agents dithiotreitol and mercaptoethanol.

2. Dipeptidase as claimed in claim 1, obtained from lactic acid streptococci.

3. Dipeptidase as claimed in claim 1, obtained from Streptococcus cremoris.

4. Dipeptidase as claimed in claim 1, obtained from Streptococcus cremoris Wg2.

5. A process as claimed in claim 1, in which a DEAE-Sephacel column is used as the ion exchange chromatographic column, and said fractions are obtained by gradient elution.

6. A process as claimed in claim 5, in which a preparative polyacrylamide gel electrophoresis is performed in a column and the effluent from the column is collected in fractions.

7. The use of the dipeptidase as claimed in claim 1 for preparing polyclonal or monoclonal antibodies having an affinity to and/or specificity for, the dipeptidase.

8. Polyclonal and monoclonal antibodies having an affinity to and/or specificity for, the dipeptidase as claimed in claim 1.

9. The use of polyclonal or monoclonal antibodies as claimed in claim 8 for detecting the dipeptidase in, or removing or isolating it from, a mixture containing the dipeptidase.

10. The use of the dipeptidase as claimed in claims 1 in the production of food products, such as cheese, beatable products and meat products.

11. Food products, such as cheese, beatable products and meat products, produced using the dipeptidase as claimed in claim 1.

12. A process for isolating a dipeptidase as claimed in claim 1 from lactic acid bacteria which comprises preparing a cell-free extract of the lactic acid bacteria by lysis of the cells and removal of the particulates, subjecting the cell-free extract to ion exchange column chromatography, selecting one or more fractions having leucyl-leucine hydrolyzing activity from the eluate of the ion exchange column, subjecting said fractions to electrophoresis and recovering one or more fractions having leucyl-leucine hydrolyzing activity from the eluate of the electrophoresis.

* * * * *